(12) United States Patent
Southwell

(10) Patent No.: US 8,200,448 B2
(45) Date of Patent: Jun. 12, 2012

(54) OPTICAL MONITOR FOR RUGATE FILTER DEPOSITION

(76) Inventor: William H. Southwell, Thousand Oaks, CA (US)

( * ) Notice: Subject to any disclaimer, the term of this patent is extended or adjusted under 35 U.S.C. 154(b) by 529 days.

(21) Appl. No.: 12/322,508

(22) Filed: Feb. 3, 2009

(65) Prior Publication Data

US 2009/0216474 A1    Aug. 27, 2009

Related U.S. Application Data

(60) Provisional application No. 61/066,545, filed on Feb. 21, 2008.

(51) Int. Cl.
*G06F 19/00* (2011.01)
*G01N 21/55* (2006.01)

(52) U.S. Cl. .......... 702/85; 702/189; 702/194; 702/199; 356/239.2; 356/445; 359/591

(58) Field of Classification Search .................... 702/85, 702/189, 184, 199; 356/239.2, 445; 359/591; 351/163
See application file for complete search history.

(56) References Cited

OTHER PUBLICATIONS

Southwell, William H. "Extended-bandwidth reflector designs by using wavelets." 1997. pp. 314-318.*

* cited by examiner

*Primary Examiner* — Sujoy Kundu

(57) ABSTRACT

This invention describes a means to monitor the deposition of a rugate filter such that the deposited filter will have the specified bandwidth, angular shift properties, and the correct wavelength of the reflectance peak.

10 Claims, 3 Drawing Sheets

Layer thickness monitor for a vacuum deposition chamber.

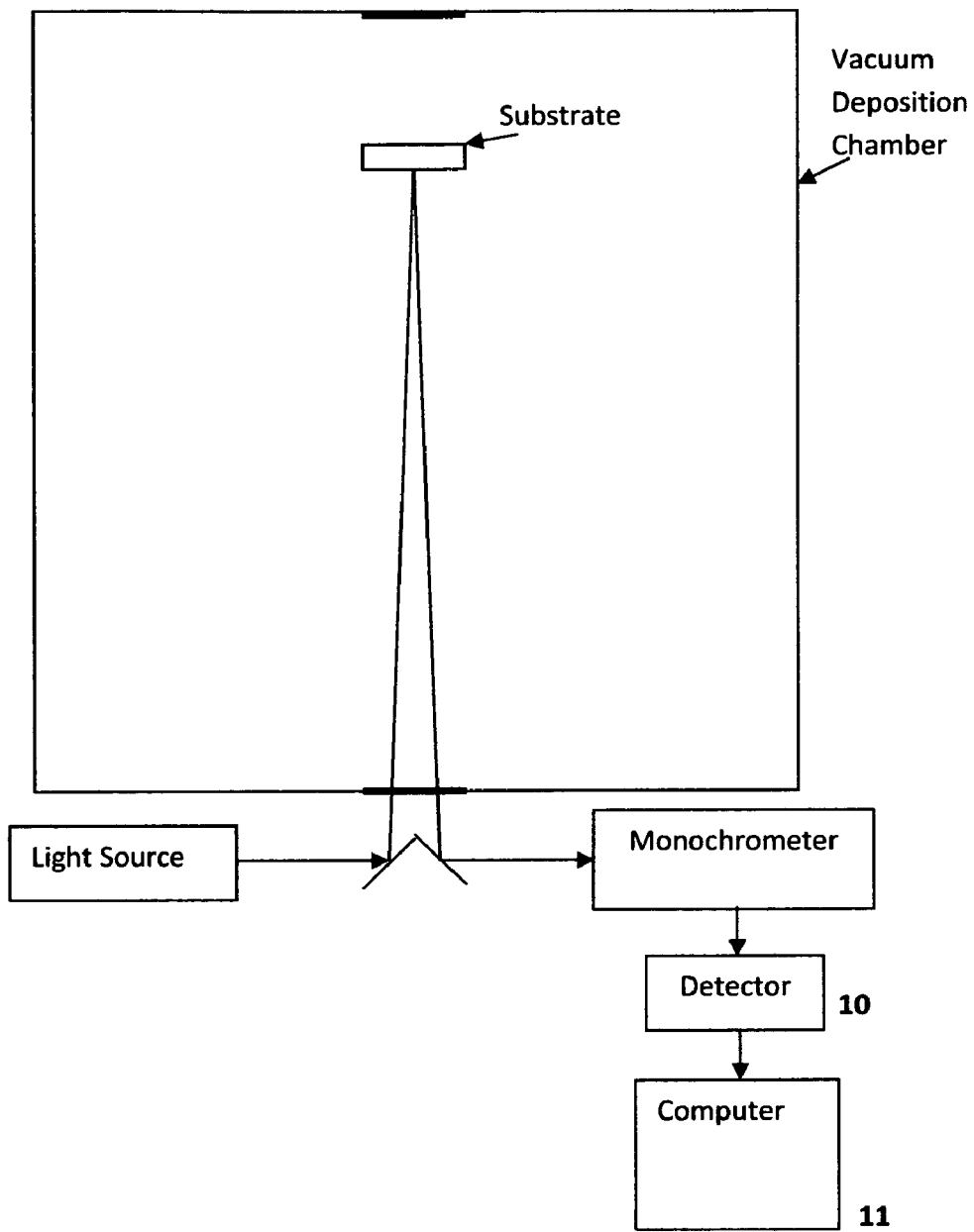
Figure 1. Layer thickness monitor for a vacuum deposition chamber.

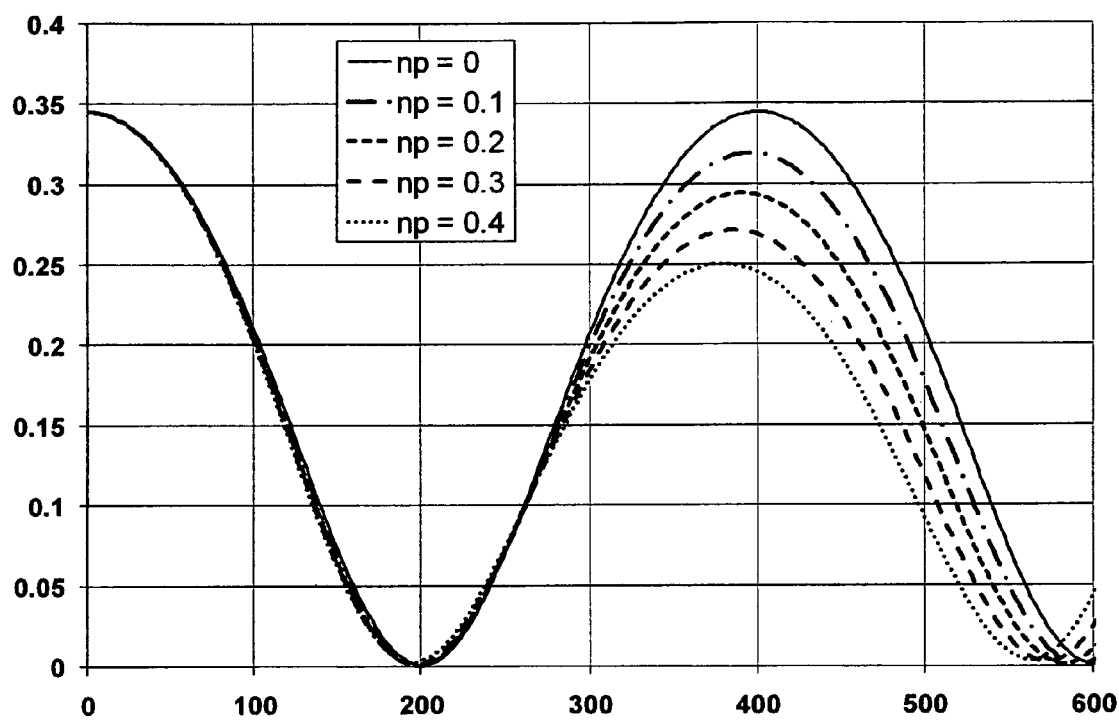
Figure 2. Reflectance monitor signal at $\lambda_M$ = 800 nm for a rugate line at $\lambda_r$ =1000 nm for various rugate amplitudes as a function of deposited optical thickness. $n_a$ = 1.9.

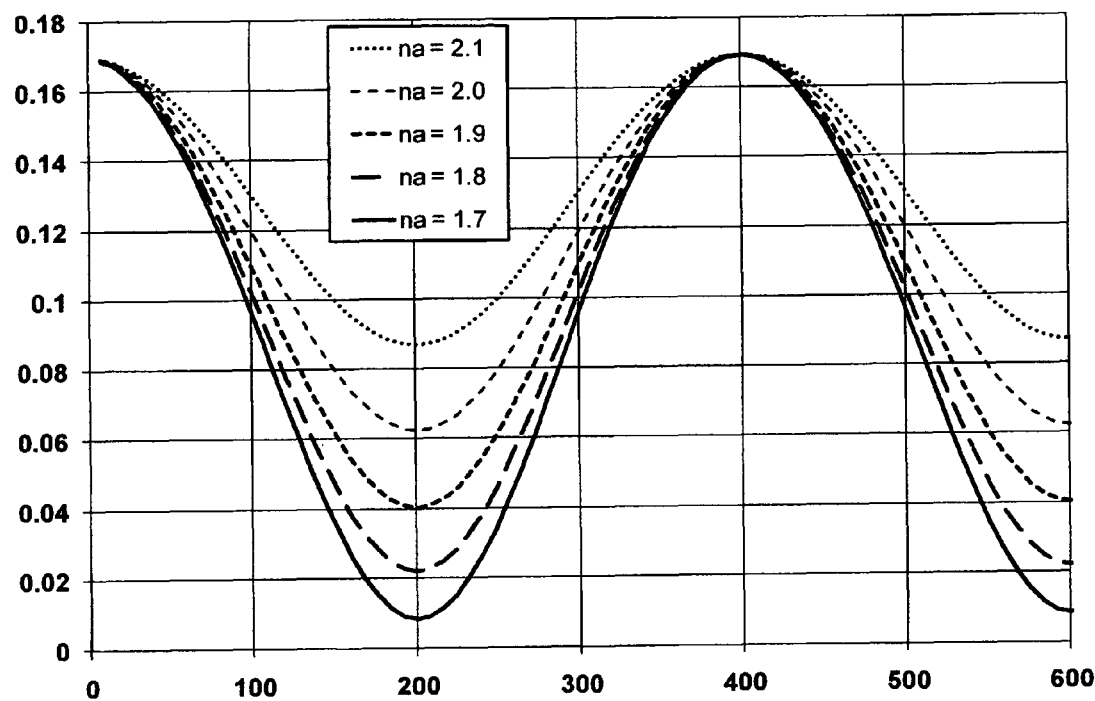
Figure 3. Monitor reflectance history for various levels of na with np = 0 and ns = 2.4.

OPTICAL MONITOR FOR RUGATE FILTER DEPOSITION

CROSS-REFERENCE TO RELATED APPLICATIONS

This application claims the benefit of provisional patent application No. 61/066,545 to William H. Southwell, filed Feb. 21, 2008.

STATEMENT REGARDING FEDERALLY SPONSORED RESEARCH OR DEVELOPMENT

This invention was made with Government support under contract FA8650-04-C-5416 awarded by U.S. Air Force to Rugate Technologies, Inc. The Government has certain rights in the invention.

FIELD OF THE INVENTION

This invention relates to the deposition of thin films used, for example, in optical filters and to thickness monitoring and thickness error correction of such layers. In particular, this invention relates to the deposition of gradient index thin films or rugate filters.

BACKGROUND OF THE INVENTION

This invention is a new approach for monitoring the deposition of a rugate filter. It is an optical monitor using as few as one cycle reflectance (or transmittance) of the deposited rugate refractive index. This approach yields all of the three basic parameters of the rugate cycle: the average index, the peak-to-peak index variation, and the wavelength position of the rugate stop band. The basic features of this monitor are described, but not necessarily all the implementations of the use of this method. Once the fundamental concepts are understood several embodiments become obvious to one skilled in thin film filter deposition. Optical interference filters typically consist of alternating thin films of high and low refractive index. The thicknesses of these layers are important in order to achieve the desired spectral properties of the filter, such as its reflectance and transmittance. The design thicknesses are important to achieve in the filter in order to obtain the spectral features of the filter design. Typically layer thicknesses are monitored. Sometimes when the layer being deposited has a known and stable deposition rate, the deposition may be terminated by using a clock to time the deposition duration. Many factors determine the layer thickness accuracy. Layer source material may change its evaporation rate due to source depletion or surface changes, for example. In this case layer thickness monitors are used to terminate the deposition to achieve the required layer thickness. The current state of the art in the monitoring of thin films is given in books such as *Thin-Film Optical Filters*, by H. A. Macleod, Taylor & Francis Group (2001); *Optical Coating Technology* by Philip W. Baumeister, SPIE Press (2004); and *Practical Monitoring and Control of Optical Thin Films* by Ronald R. Willey, Willey Optical, Consultants (2007).

There are two types of thin film monitors in general use: crystals and optical monitors. Crystals measure the weight of the deposition on a small quartz crystal by looking at the change in frequency of its resonant oscillations. Crystals can become noisy, especially after accumulating much material, and become less reliable. Optical monitors use wave front interference of a projected light beam on a depositing part to deduce its optical thickness. Optical thickness is the product of the physical thickness of the layer and its refractive index. When the refractive index of the deposited material is known (as is typically the case for most optical filters using alternating layers of high and low refractive index layers), the physical thickness is inferred. Some high performance filters such as those used in telecom applications (very narrow band filters) are manufactured using optical monitoring.

Rugate Filters

Neither of the current types of deposition monitors are particularly effective when depositing rugate filters. The reason is that the refractive index in a rugate filter is not fixed, but is constantly changing. A rugate filter consists of a sinusoidal refractive index profile, rather than alternating high and low refractive index layers using two materials. When z is the optical thickness depth of a rugate filter, the refractive index for a rugate filter is, $$n(z)=n_a+0.5n_p \sin(2\pi z/\lambda_r),  \quad (1)$$

where $n_a$ is the average refractive index, $n_p$ is the full amplitude of the sinusoidal index variation, and $\lambda_r$ is the wavelength position of the resulting rugate stop band. A filter having a varying refractive index is sometimes called a gradient index optical filter. The sinusoidal refractive index is achieved by co-evaporating a high and a low refractive index material while carefully adjusting the deposition rates. This is described in U.S. Pat. No. 4,934,788, Deposition of gradient index coatings using coevaporation with rate control, William H. Southwell inventor, and U.S. Pat. No. 5,000,575, Method of fabricating gradient index optical films, William H. Southwell and Randolph L. Hall inventors.

The prior art of deposition of rugate filters includes a method using a broad band optical monitor to obtain the current total optical thickness of the deposition. This total optical thickness is used to adjust the next incremental refractive index level using Eq. (1). This is described in U.S. Pat. No. 5,425,964, Deposition of multiple layer thin films using a broad band spectral monitor, William H. Southwell and Randolph L. Hall inventors. Adjusting the sinusoidal refractive index on the basis of the current total optical thickness assures the filter's period as seen in Eq. (1). This means that the broad band spectral monitor is good for achieving the correct wavelength placement of the rugate stop band.

Shortcomings of the Prior Art

Although the optical thickness monitor of the previous art controls $\lambda_r$ (the wavelength position of the rugate line), it reveals nothing about the average index $n_a$ and sinusoidal amplitude $n_p$. These parameters of the rugate refractive index are important because $n_a$ determines the spectral shift with angle of incidence and $n_p/n_a$ determines the band width of the rugate line. [See "Spectral response calculations of rugate filters using coupled-wave theory," by W. H. Southwell, Journal of the Optical Society of America A, Vol. 5, pp 1558-1564 (1988)]

A rugate line centered at $\lambda_r$ at normal incidence will shift to lower wavelengths with increasing angle of incidence according to, $$\lambda=\lambda_r\{1-(\sin \theta/n_a)^2\}^{1/2},  \quad (2)$$

where $\theta$ is the angle of incidence of the light. The bandwidth B of the rugate line is given by, $$B=\Delta\lambda/\lambda=n_p/(2n_a).  \quad (3)$$

Filters fabricated using the optical monitor often have the correct line position but will have incorrect bandwidth and angle sensitivities.

What is needed is a monitor that will reveal the rugate average index na as well as the sinusoidal amplitude np in addition to the period of the sinusoidal refractive index variation.

BRIEF SUMMARY OF THE INVENTION

I have discovered that the reflectance history of a single line optical monitor of a single rugate cycle (or less or more) can be used to deduce all three essential parameters of the rugate refractive index. These parameters are described in Eq. (1) and are, $n_a$ the average refractive index, $n_p$ the sinusoidal amplitude of the refractive index, and $\lambda_r$ the period of the sinusoidal refractive index.

The monitor wavelength relative to the rugate line center is not particularly important. Monitoring on the rugate line center can be used to obtain optical thickness, particularly quarter wave segments of optical thickness since they are determined by the reflectance peaks or valleys. (This is a standard method for depositing quarter wave stack filters.) However, in this invention one may monitor off line and obtain a signal that is indicative of $n_a$ and $n_p$ of the rugate refractive index as well as the line position of the rugate filter.

BRIEF DESCRIPTION OF THE DRAWINGS

In the drawings:

FIG. 1 is a schematic view of a vacuum deposition chamber used to deposit optical thin films.

FIG. 2 is a plot of an example optical monitor signal for layers with differing rugate sine wave index amplitudes.

FIG. 3 is a plot of an example optical monitor signal for layers with differing average rugate index.

DETAILED DESCRIPTION OF THE DRAWINGS

The filter substrates are typically placed near the top of the chamber as shown in FIG. 1. An optical beam is directed onto one of the filters being deposited and then directed to an optical filter or monochrometer which selects the monitor wavelength. The beam is then directed to the detector 10 where the light intensity is measured and sent to a computer. The computer also records the time at which the measurement was made.

To get a better picture of how this approach works, consider the single wavelength optical monitor signal shown in FIG. 2. The value of the best fit second extreme of the monitor signal relative to the starting value is a measure of the rugate index sine wave amplitude, $n_p$. Now consider the monitor signal shown in FIG. 3. The value of the best fit first extreme of the monitor signal, when the substrate index is not near the square of the average rugate index, is a measure of the average rugate index, $n_a$. The optical thickness position of the first extreme is a measure of the rugate line wavelength.

DESCRIPTION OF THE INVENTION

Consider the reflectance history plots shown in FIG. 2. The refractive index being deposited (in simulation) is $n_a$=1.9, and the rugate line center is $\lambda_r$=1000 nm. The monitor wavelength $\lambda_M$ is 800 nm. The monitor chip or substrate refractive index is $n_s$=3.85 (corresponding to Si). The monitor signal for two rugate cycles is shown.

It is clear from FIG. 2 that the reflection level of the first reflectance maximum relative to the initial reflection level is a good indication of the amplitude of the sine wave index being deposited. Similar simulations were run for various values of $n_a$. These simulations revealed a problem when the average rugate index is approximately the square root of the refractive index of the monitor substrate. A zero reflectance minimum occurs with this layer index. Layers with index just lower or higher than this will give the same non-zero reflectance dip. However, we may avert this ambiguity by choosing another substrate material, as we did in FIG. 3, where we chose a substrate of ns=2.4 (corresponding to ZnSe). It is clear from FIG. 3 that the reflection level of the first reflectance minimum relative to the initial reflection is a good indication of the rugate average refractive index.

Clearly these monitor plot histories contain information about $n_a$ and $n_p$. There are several ways to extract this information. One could record the value of the first dip and the first peak and use "look-up" tables to surmise the parameters. These values could be normalized by the beginning reflectance to reduce the effects of some systematic errors.

Another approach is to use the accumulated reflectance data and fit it to a calculated reflectance from a parameterized refractive index profile given in Eq. (1). This approach has been shown to produce robust estimates simultaneously for both $n_a$ and $n_p$.

Other approaches may also become evident to those skilled in the art. Such embodiments are included within the scope of this invention, including the use multiple monitor wavelengths.

If the optical thickness is known then the least squares approach also produces $\lambda_r$ the rugate line wavelength position. However, in practice the abscissa may be time which is related to the optical thickness through the deposition rates of both materials. The time between two turning points $\tau_{TP}$ (seconds) will be the time required to deposit one half wave optical thickness at the monitor wavelength $\lambda_M/2$ (nm). (A half wave optical thickness at the wavelength of the rugate line position corresponds to a full rugate cycle.) Thus, when the deposition rate is uniform or when its variation can be accounted for, the reflectance history period in seconds that is fit with the least squares procedure may be converted to the rugate line position according to, $$\lambda_r = \lambda_M P_{qw}/\tau_{TP}, \tag{4}$$

where $P_{qw}$ is the best fit period in seconds in the model given by Eq. (1).

DETAILED DESCRIPTION OF THE PREFERRED EMBODIMENT

To clarify the operation of the monitor, we present the following steps.

1. An optical beam of light having wavelength $\lambda_M$ is incident on a substrate receiving the rugate deposition having arbitrary values of $n_a$, $n_p$, and $\lambda_r$, according to, $$n(z) = n_a + 0.5 n_p \sin(2\pi z/\lambda_r), \tag{5}$$

where z is the optical thickness depth parameter of the deposited coating.

2. The reflection R of this beam is recorded along with the current optical thickness (or time) in arrays xD, yD while the deposition of the rugate proceeds.

$$xD(i) = OT_i, yD(i) = R_I \tag{6}$$

3. This data is then fit with a least squares algorithm to a function that evaluates the reflectance as a function of optical thickness from a refractive index profile given by, $$n(x) = v_1 + 0.5 v_2 \sin(2\pi x/v_3), \tag{7}$$

where $v_1$ is the fit parameter for the average refractive index $n_a$, $v_2$ is the fit parameter for the peak-to-peak amplitude refractive index $n_p$, and $v_3$ is the fit parameter for the rugate line position $\lambda_r$. A standard way to evaluate the reflectance R at wavelength $\lambda_M$ is to consider each deposited increment as a thin layer of constant refractive index and use the characteristic matrix for thin films.

The fit parameters are the desired estimates, $$n_a = v_1$$

$$n_p = v_2$$

$$\lambda_r = v_3. \quad (8)$$

The above fitting approach has been constructed and tested using simulated deposition data. The process has proven to be robust even in the presence of random noise.

An important result is that the rugate line position (or all the rugate parameters) may be determined when monitoring on-line or off-line of the rugate wavelength. This surprising result adds utility to this method. Sometimes it is difficult or impossible to monitor at the rugate line. It also allows the use of standard inexpensive lasers or other light sources to be used as a monitor source.

This invention fills a definite need in rugate technology. Rugate filters have many important applications, but their construction has eluded many including reputable optical coating suppliers. Rugate filters are often very thick and require long deposition times. The lack of a monitor to determine how well the rugate parameters are being achieved during a rugate deposition run is one reason for the lack of industrial progress in this area. This invention will allow the construction of higher performance rugate filters with controlled bandwidths and angle sensitivities.

The invention claimed is:

1. An optical monitor for the deposition of rugate filters consisting of a single wavelength incident beam on a selected substrate receiving the deposition stream which allows the reflectance variations to be saved as the deposition proceeds and which reflection data is then fit to a calculated monitor signal using a refractive index model the fit parameters of which determine the estimates for the rugate average index $n_a$ and the amplitude of the index variations $n_p$.

2. An optical monitor of claim 1 which also determines the wavelength of the rugate line position.

3. An optical monitor of claim 1 which determines the rugate parameters by using a monitor wavelength that is on-line or off-line to that of the line position of the rugate filter being deposited.

4. An optical monitor of claim 1 for the determination of rugate parameters in which the rugate parameters may be determined with the deposition of only approximately one rugate cycle or less.

5. An optical monitor of claim 1 for the determination of the parameters of a rugate filter during deposition consisting of collecting reflection monitoring data during deposition and applying least squares algorithms to estimate the parameters of the rugate index profile.

6. A method for the deposition of rugate filters consisting of a single wavelength incident beam on a selected substrate receiving the deposition stream which allows the reflectance variations to be saved as the deposition proceeds and which reflection data is then fit to a calculated monitor signal using a refractive index model the fit parameters of which determine by a computer the estimates for the rugate average index $n_a$ and the amplitude of the index variations $n_p$.

7. A method of claim 6 which also determines the wavelength of the rugate line position.

8. A method of claim 6 which determines the rugate parameters by using a monitor wavelength that is on-line or off-line to that of the line position of the rugate filter being deposited.

9. A method of claim 6 for the determination of rugate parameters in which the rugate parameters may be determined with the deposition of only approximately one rugate cycle or less.

10. A method of claim 6 for the determination of the parameters of a rugate filter during deposition consisting of collecting reflection monitoring data during deposition and applying least squares algorithms to estimate the parameters of the rugate index profile.

* * * * *